United States Patent [19]

Aizawa et al.

[11] Patent Number: 6,153,708
[45] Date of Patent: Nov. 28, 2000

[54] HIGHLY POLYMERIZABLE N-VINLYCARBOXYLIC ACID AMIDE AND PRODUCTION PROCESS THEREOF

[75] Inventors: Toshiyuki Aizawa; Hitoshi Nakamura; Tetsuo Kudo; Kunitoshi Wakabayashi; Kenji Shimamura; Shun-ichi Nagamatsu, all of Oita, Japan

[73] Assignee: Showa Denko Kabushiki Kaisha, Tokyo, Japan

[21] Appl. No.: 09/271,428

[22] Filed: Mar. 18, 1999

Related U.S. Application Data

[62] Division of application No. 08/996,819, Dec. 23, 1997, Pat. No. 5,892,115, which is a division of application No. 08/585,919, Jan. 16, 1996, Pat. No. 5,789,619.

[51] Int. Cl.[7] .................................................. C08F 283/04
[52] U.S. Cl. .......................... 525/420; 525/419; 525/421; 525/425; 525/426; 525/432; 525/436
[58] Field of Search ..................................... 525/419, 420, 525/421, 425, 426, 432, 436

[56] References Cited

U.S. PATENT DOCUMENTS

| | | |
|---|---|---|
| 4,018,826 | 4/1977 | Gless, Jr. et al. . |
| 4,554,377 | 11/1985 | Stackman et al. . |
| 5,280,095 | 1/1994 | Aizawa et al. . |

FOREIGN PATENT DOCUMENTS 3938016  11/1988  Germany .

OTHER PUBLICATIONS

Abstracts of Japan, JP 8081428, Mar. 1996.
Beilstein 5860055, 1993.
Beilstein 3536196, 1990.
Beilstein 1811739, 1966.
Beilstein 2203670, 1963.
Beilstein 1849327, 1972.
Beilstein 1743331, 1939.
Beilstein 1811672, 1980.
Beilstein 1848006, 1966.
Beilstein 1847279, 1966.
Journal of the American Chemical Society, Sep. 16, 1976.

*Primary Examiner*—Shailendra Kumar
*Attorney, Agent, or Firm*—Sughrue, Mion, Zinn, Macpeak & Seas, PLLC

[57] ABSTRACT

A highly polymerizable N-vinylcarboxylic acid amide having an N-1,3-butadienylcarboxylic acid amide content of 30 ppm or less, a process for producing the same, and a process for producing a homopolymer of N-vinylcarboxylic acid amide or a copolymer thereof with another copolymerizable monomer using the same. Also, a highly polymerizable N-vinyl-carboxylic acid amide is produced by thermal cracking or catalytic cracking of N-(1-alkoxyethyl) carboxylic acid amide or ethylidenebiscarboxylic acid amide, wherein the N-vinyl-carboxylic acid amide content of the N-(1-alkoxyethyl)-carboxylic acid amide or ethylenebiscarboxylic acid amide is 10 wt % or less.

2 Claims, 1 Drawing Sheet

N - 1, 3 - butadienylacetamide content (wt. ppm)
of Crude N - vinylacetamide (NVA)

HIGHLY POLYMERIZABLE N-VINLYCARBOXYLIC ACID AMIDE AND PRODUCTION PROCESS THEREOF

This is a divisional of application Ser. No. 08/996,819, filed Dec. 23, 1997, now U.S. Pat. No. 5,892,115, which is a divisional of application Ser. No. 08/585,919, filed Jan. 16, 1996, now U.S. Pat. No. 5,789,619, the disclosure of which is incorporated herein by reference.

FIELD OF THE INVENTION

The present invention relates to a highly polymerizable N-vinylcarboxylic acid amide, a production process thereof and a process for producing a high molecular weight polymer of N-vinylcarboxylic acid amide using the same. More specifically, the present invention provides an N-vinylcarboxylic acid amide having improved polymerizability and a process for producing the same. The N-vinylcarboxylic acid amide is advantageously used in industry as a monomer for the production of an N-vinylcarboxylic acid amide polymer, which polymer is used as a coagulant, a liquid absorbent or a thickener. The present invention also provides a process for producing the polymer. Furthermore, the present invention provides a high-quality N-vinylcarboxylic acid amide that is useful as a raw material for industrial chemicals or medical products in various fields.

BACKGROUND OF THE INVENTION

A large number of methods for producing an N-vinylcarboxylic acid amide have hitherto been proposed. For example, a method is known where an N-(1-alkoxyethyl)-carboxylic acid amide as an intermediate is produced from a carboxylic acid amide, acetaldehyde and an alcohol, and an N-vinylcarboxylic acid amide is synthesized by cracking or catalytic cracking of the product. Another useful method for synthesizing an N-vinylcarboxylic acid amide includes synthesizing an ethylidene biscarboxylic acid amide from acetaldehyde and a carboxylic acid amide. This product is then cracked into a carboxylic acid amide and an N-vinylcarboxylic acid amide.

In these methods, a purification step, such as distillation, extraction and recrystallization of the resulting N-vinylcarboxylic acid amide is provided. For example, JP-A-61-286069 (the term "JP-A" as used herein means an "unexamined published Japanese patent application") discloses an extraction separation using water and an aromatic hydrocarbon. This is because distillation fails to prevent mingling of formamide as an unreacted raw material into the N-vinylformamide. Furthermore, JP-A-63-132868 discloses cooling crystallization from a mixed organic solvent, JP-A-2-188560 discloses extraction using an aqueous inorganic salt solution and an aromatic hydrocarbon, and U.S. Pat. No. 4,401,516 discloses extractive distillation using a polyhydric alcohol.

On the other hand, an N-vinylcarboxylic acid amide polymer is obtained by polymerizing an N-vinylcarboxylic acid amide alone or copolymerizing with another monomer. The polymer is used as a coagulant, a liquid absorbent or a thickener, and in any case the polymer must have a high molecular weight. However, it has been difficult to obtain an N-vinylcarboxylic acid amide which consistently exhibits good polymerizability in any of the uses described above.

SUMMARY OF THE INVENTION

An object of the present invention is to provide a highly polymerizable N-vinylcarboxylic acid amide having good and improved polymerizability.

Another object of the present invention is to produce a high molecular weight N-vinylcarboxylic acid amide polymer.

As a result of extensive investigations on the production process of an N-vinylcarboxylic acid amide having good polymerizability, the present inventors have found that a high molecular weight polymer can be produced using an N-vinylcarboxylic acid amide having an N-1,3-butadienylcarboxylic acid amide content of 30 ppm or less, preferably 10 ppm or less, more preferably 1 ppm or less, to thereby achieve the present invention.

More specifically, the present invention provides a highly polymerizable N-vinylcarboxylic acid amide, wherein the N-vinylcarboxylic acid amide has an N-1,3-butadienylcarboxylic acid amide content of 30 ppm or less, a production process thereof, and a process for producing a high molecular weight polymer of an N-vinylcarboxylic acid amide using the same.

DETAILED DESCRIPTION OF THE INVENTION

Figure 1:
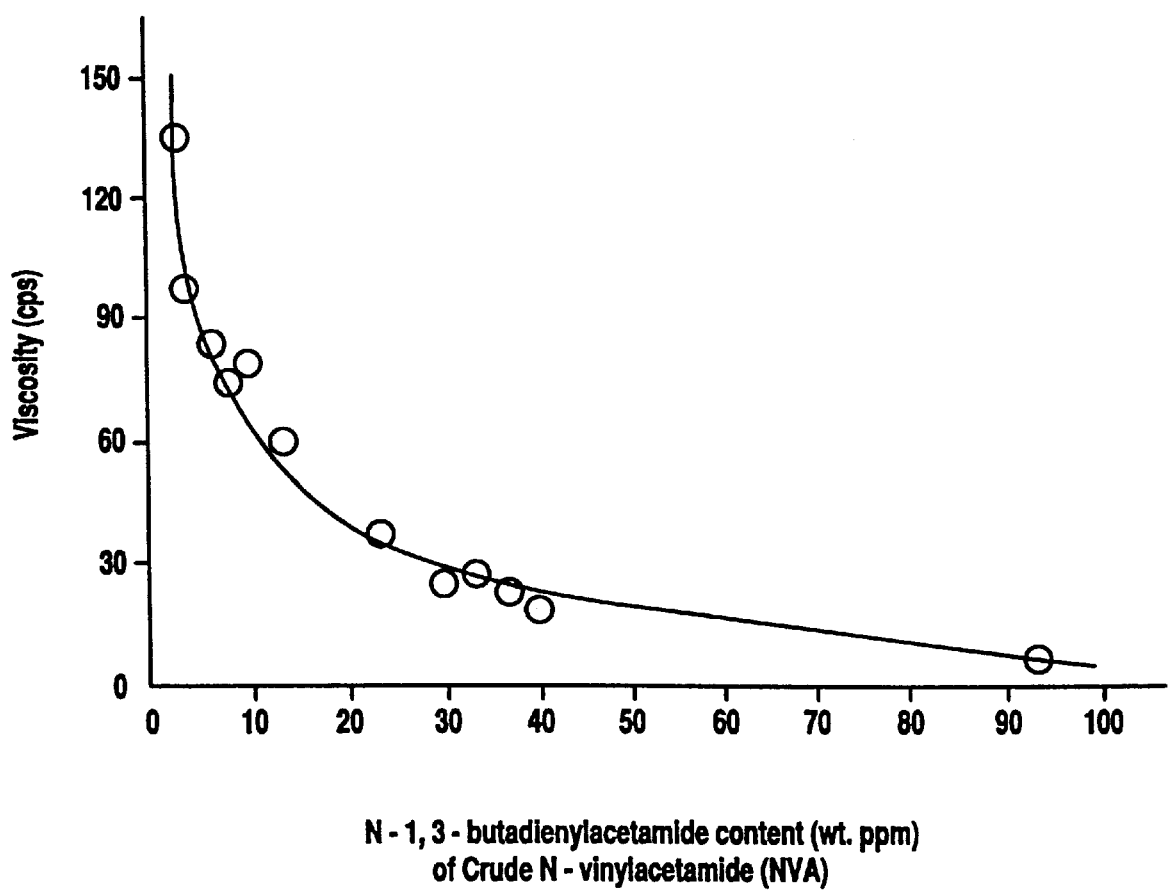
FIG. 1 shows the relationship between viscosity and the N-1,3-butadienylacetamide content of crude N-vinylacetamide (NVA) as measured following the procedure of Example 1. The viscosity is a measure of the degree of polymerizability.

The present invention is described in detail below.

The N-vinylcarboxylic acid amide for use in the present invention is represented by formula (I):

$$CH_2=CH-NR^1-COR^2 \qquad (I)$$

(wherein R' and R each represents a hydrogen atom or an alkyl group having from 1 to 5 carbon atoms). Examples thereof include N-vinylformamide, N-methyl-N-vinylformamide, N-vinylacetamide, N-methyl-N-vinylacetamide, N-vinylpropionamide, N-methyl-N-vinylpropionamide, N-vinylbutylamide and N-vinylisobutylamide. Among these, N-vinylformamide and N-vinylacetamide are preferred and N-vinylacetamide is more preferred.

The N-1,3-butadienylcarboxylic acid amide is represented by formula (II):

$$CH_2=CH-CH=CH-NR^1-COR^2 \qquad (II)$$

(wherein $R^1$ and $R^2$ each has the same meaning as defined above) and includes cis and trans forms which are present as geometrical isomers thereof.

In the present invention, a highly polymerizable N-vinylcarboxylic acid amide is obtained by setting the content of N-1,3-butadienylcarboxylic acid amide in the crude N-vinylcarboxylic acid amide to 30 ppm or less, but a desired high polymerizability may be obtained by setting the content preferably to 10 ppm or less, and more preferably to 1 ppm or less. If the content exceeds the above-described range, high polymerizability is difficult to achieve.

This is verified, for example, by the relationship (FIG. 1) between the content of N-1,3-butadienylacetamide in crude N-vinylacetamide and viscosity (degree of polymerizability).

There is no particular limitation on the production process of an N-vinylcarboxylic acid amide which is used in the process for producing a highly polymerizable N-vinylcarboxylic acid amide of the present invention, as long as the crude N-vinylcarobxylic acid amide thus obtained has an N-1,3-butadienylcarboxylic acid amide content in excess of 30 ppm, and in some cases, in excess of 10 ppm or 1 ppm. However, in one preferred embodiment, the N-vinylcarboxylic acid amide is produced through dealcoholization of an N-(1-alkoxyethyl)carboxylic acid amide or dealcoholization of an N-(1-alkoxyethyl)carboxylic acid amide obtained as an intermediate from carboxylic acid amide, acetaldehyde and alcohol or from carboxylic acid amide and acetaldehyde dialkylacetal. In this case, the dealcoholization reaction is preferably conducted by thermal cracking or catalytic cracking. In another preferred embodiment, the N-vinylcarboxylic acid amide is produced through cracking of ethylidene biscarboxylic acid amide or cracking of an ethylidene biscarboxylic acid amide obtained as an intermediate from acetaldehyde and carboxylic acid amide. In this case, the ethylidene biscarboxylic acid is cracked into a carboxylic acid amide and an N-vinylcarboxylic acid amide. In the present invention, a highly polymerizable N-vinylcarboxylic amide having an N-1,3-butadienylcarboxylic acid amide content of 30 ppm or less may be produced by a purification processing method where an N-1,3-butadienylcarboxylic acid amide is reduced or removed from the crude N-vinylcarboxylic acid amide, or by a purification processing method where an N-1,3-butadienylcarboxylic acid amide or a precursor thereof is reduced or removed from the production raw material or intermediate of N-vinylcarboxylic acid amide.

A method of reducing or removing an N-1,3-butadienylcarboxylic acid amide from the crude N-vinylcarboxylic acid amide is described below.

The purification processing method for reducing or removing an N-1,3-butadienylcarboxylic acid amide from the crude N-vinylcarboxylic acid amide includes, for example, a physical purification processing method of processing the crude N-vinylcarboxylic acid amide or a solution thereof by rectification, a recrystallization method, pressure crystallization or treatment with an adsorbent such as activated carbon, and a purification processing method using chemical conversion of N-1,3-butadienylcarboxylic acid amide, such as a method of processing N-1,3-butadienylcarboxylic acid amide with p-benzoquinone using a Diels-Alder reaction and a method of processing the 1,3-butadienyl group using selective hydrogenation. These methods may be used either individually or in combination. Other than the above-described methods, any method may be used if the N-1,3-butadienylcarboxylic acid amide is easily separated from the N-vinylcarboxylic acid amide or chemically converted.

The method for removing or reducing the amount of N-1,3-butadienylcarboxylic acid amide from the crude N-vinylcarobxylic acid amide is described in greater detail below.

In the process of the present invention, there is no particular limitation on the distillation apparatus for use in separating by rectification, and a plate column or packed column having a theoretical plate number of from 1 to 50 may be used. However, a rectifying column is preferably used which causes little pressure loss and has excellent rectifiability, and examples thereof include a packed column using a regular filling. The distillation is preferably conducted at a temperature that is as low as possible because the N-vinylcarboxylic acid amide is readily deteriorated due to heat. Accordingly, the distillation is conducted under a reduced pressure of from 0.01 to 100 mmHg.

The rectification may be conducted either continuously or discontinuously, however, a continuous operation is preferred in view of productivity and safety in operation. The reflux ratio is not particularly limited and can be set according to the content of N-1,3-butadienylcarboxylic acid amide, the kind of N-vinylcarboxylic acid amide and the capabilities of the distillation column. However, the reflux ratio is generaly from 0.1 to 20, and preferably from 0.5 to 10.

In the process of the present invention, when the separation is made by a recrystallization method comprising cooling a crude N-vinylcarboxylic acid amide, the N-vinylcarboxylic acid amide may be directly cooled, or a recrystallization solvent which does not react with the N-vinylcarboxylic acid amide and having an appropriate solubility may be used. Examples of the recrystallization solvent include an aromatic hydrocarbon such as benzene, toluene and xylene; an aliphatic hydrocarbon such as pentane, cyclopentane, hexane, cyclohexane and heptane; an alcohol such as methanol, ethanol, n-propyl alcohol, isopropyl alcohol, n-butanol, isobutanol, sec-butanol, tert-butanol and cyclohexanol; a halogenated hydrocarbon such as chloroform and chlorobenzene; a ketone such as acetone, methyl ethyl ketone and cyclohexanone; an ester such as methyl acetate, ethyl acetate, propyl acetate and butyl acetate; an ether such as diethyl ether; an amide such as N,N-dimethylformamide and N,N-dimethylacetamide; and a dimethylsulfoxide. Toluene, cyclohexane, methanol and isopropyl alcohol are preferred. These solvents may also be used in combination. The cooling temperature varies depending upon the kind and the amount of the N-vinylcarboxylic acid amide and the recrystallization solvent, but it is usually from −20 to 50° C., preferably from −10 to 40° C.

The crystallization apparatus for use in the present invention is not particularly limited with respect to its structural form and may be either a continuous system or a batch system. Also, the crystallization method may either employ heat exchange with a cooling medium, or concentration and cooling of the solvent upon evaporation.

The apparatus for separating crystals for use in the present invention is also not particularly limited. An apparatus using vacuum pressure or the application of pressure, or an apparatus using gravity or centrifugal force may be used.

In the present invention, a solid-liquid separator which combines crystallization and separation in the same apparatus may also be used. Preferred examples of the apparatus include, in the case of not using a crystallization solvent, a pressure crystallizer, a falling film crystallizer (e.g., a fractional crystallization apparatus) and a tower type continuous crystallization purifier (e.g., a BMC or back mixing column crystallizer apparatus). In the case of filtering a high concentration slurry, an automatic Nutsche filter such as a Rosemund filter is preferably used.

In the process of the present invention, when the crude N-vinylcarboxylic acid amide is separated by treating with an adsorbent such as activated carbon, the adsorbent for use in the present invention is not particularly limited as long as it selectively adsorbs the N-1,3-butadienylcarboxylic acid amide in comparison with the N-vinylcarboxylic acid amide. Examples of the adsorbent include activated carbon, clays, alumina, silica, zeolite and adsorptive resin, and among these, activated carbon is preferred.

In the adsorption operation of the present invention, the crude N-vinylcarboxylic acid amide may be placed into direct contact with the adsorbent. Alternatively, the crude solution may be dissolved in a solvent which does not react with the N-vinylcarboxylic acid amide and which has an appropriate solubility, and then placed into contact with the adsorbent. Examples of the solvent include water and those described above with respect to the method of recrystallization, and when activated carbon is used as an adsorbent, water and methanol are particularly preferred. The ratio of the solvent to the crude N-vinylcarboxylic acid amide is not particularly limited, however, when water or methanol is used as the solvent, it is preferably from 0 to 10:1 (by weight), more preferably from 0.1 to 3:1 (by weight).

The adsorption temperature suitable for conducting the adsorption operation of the present invention varies depending upon the kind of adsorbent, but it is preferably from −20 to 100° C., more preferably from 0 to 80° C. If the adsorption temperature is lower than −20° C., diffusion into the pores of the adsorbent is considerably retarded to disadvantageously prolong the adsorption time. If the temperature is higher than 100° C., stability of the N-vinylcarboxylic acid amide is lowered and at the same time, the equilibrium adsorption quantity is greatly reduced.

The adsorption method of the present invention is not particularly limited with respect to the structural form thereof, but may either be a continuous system or a batch system.

In the present invention, the content of N-1,3-butadienylcarboxylic acid amide in the N-vinylcarboxylic acid amide may be reduced to 30 ppm or less by chemically processing the crude N-vinylcarboxylic acid amide solution. There is no particular limitation on the chemical reaction to be used as long as it uses the difference in reactivity between the N-vinylcarboxylic acid amide and the N-1,3-butadienylcarboxylic acid amide. For example, the reaction with a diene is highly active but the reaction with a monoene is inactive.

The method of processing the crude N-vinylcarboxylic acid amide solution using a Diels-Alder reaction, and the method of processing the solution using selective hydrogenation are described below.

In the present invention, when the crude N-vinylcarboxylic acid amide solution is processed using a Diels-Alder reaction, the processing is conducted by allowing a dienophilic compound (dienophile) in the Diels-Alder reaction to be present in the crude N-vinylcarboxylic acid amide solution. The dienophilic compound of the present invention is not particularly limited as long as it is a compound commonly used as a dienophilic compound in the Diels-Alder reaction, more specifically, a compound which is selected from α,β-unsaturated compounds substituted by one or more electron attractive group(s) and which does not react with the N-vinylcarboxylic acid amide. Examples of the dienophilic compound include an unsaturated carboxylic ester;

such as acrylic ester maleic ester and fumaric ester, an unsaturated ketone such as methyl vinyl ketone and p-benzoquinone; an unsaturated nitrile such as acrylonitrile; and an unsaturated imide such as maleic acid imide. Among these, p-benzoquinone is preferred. The amount of the dienophilic compound is not particularly limited as long as it is equivalent to or more than the amount of the N-1,3-butadienylcarboxylic acid amide contained in the crude N-vinylcarboxylic acid amide. However, the molar ratio of the dienophilic compound to the N-1,3-butadienylcarboxylic acid amide contained in the crude N-vinylcarboxylic acid amide solution is generally from 1 to 100 equivalents, and preferably from 1.2 to 10 equivalents.

In the present invention, when the crude N-vinylcarboxylic acid amide solution is processed by a Diels-Alder reaction, the crude N-vinylcarboxylic acid amide may be directly contacted with the dienophilic compound. Alternatively, the crude solution may be dissolved in a solvent which does not react with the N-vinylcarboxylic acid amide and has an appropriate solubility, and then subjected to a Diels-Alder reaction. Examples of the solvent include the solvents described above with respect to the adsorption method of the present invention. Furthermore, although a catalyst is not required when the crude N-vinylcarboxylic acid amide solution is processed by a Diels-Alder reaction in the present invention, those known to have catalytic activity in the Diels-Alder reaction and which do not react with the N-vinylcarboxylic acid amide may be used. Examples of the catalyst include Lewis acids such as aluminum trichloride, boron trifluoride and lanthanide complex.

The reaction temperature suitable for the Diels-Alder reaction of the present invention varies depending upon the kind of the dienophilic compounds used, but it is preferably from −20 to 100° C., and more preferably from 0 to 80° C. If the reaction temperature is lower than −20° C., the reaction rate is too slow, whereas if the reaction temperature exceeds 100° C., stability of the N-vinylcarboxylic acid amide is disadvantageously reduced.

The N-vinylcarboxylic acid amide solution processed by a Diels-Alder reaction of the present invention contains a Diels-Alder adduct produced by the Diels-Alder reaction, but this compound has almost no harmful effect on the polymerization of the N-vinylcarboxylic acid amide. The Diels-Alder adduct produced in the present invention has a low vapor pressure as compared with the N-1,3-butadienylcarboxylic acid amide. Accordingly, if the N-vinylcarboxylic acid amide solution is purified by distillation after processing by a Diels-Alder reaction of the present invention, the Diels-Alder adduct can be separated more easily than N-1,3-butadienylcarboxylic acid amide that is removed by distillation alone. In other words, the compound can be separated using simple distillation equipment.

The processing of the crude N-vinylcarboxylic acid amide using a hydrogenation reaction of the present invention is conducted by contacting the crude N-vinylcarboxylic acid amide with hydrogen in the presence of a catalyst. The catalyst is not particularly limited as long as it has general activity in the selective hydrogenation reaction of olefins, however, the catalyst preferably has high diene hydrogenation selectively when a monoolefin and a diene are present together. Examples of the catalyst include a Pd series, Co series or Ni—Co—Cr series metal or a modified product of these metals provided on alumina, activated carbon or silica and among these, Pd-alumina, Pd—Ag-alumina, Pd—Pb-alumina, Pd—Cr-alumina and Pd-alumina-based catalysts are preferred. When Pd is used as the metal component, the carried amount thereof is preferably from 0.001 to 5 wt %, more preferably from 0.01 to 1 wt %. If the carried amount is less than 0.001 wt %, the reaction rate is extremely slow, whereas if it exceeds 5 wt %, N-ethylacetamide resulting from hydrogenation of the N-vinylcarboxylic acid amide disadvantageously increases.

In the present invention, when the N-vinylcarboxylic acid amide is processed by a hydrogenation reaction, the N-vinylcarboxylic acid may be directly contacted with hydrogen, or may be dissolved in a solvent, which does not react with the N-vinylcarboxylic acid amide and which has an appropriate solubility, and then subjected to a hydrogenation reaction. Examples of the solvent include the solvents described above with respect to the adsorption method of the present invention. Among these, an alcohol is preferred, and methanol and isopropyl alcohol are particularly preferred. The reaction temperature suitable for the hydrogenation reaction of the present invention varies depending upon the kind of catalyst used, but it is preferably from −20 to 100° C., more preferably from 0 to 80° C. If the reaction temperature is lower than −20° C., the reaction rate is extremely slow, whereas if it exceeds 100° C., the stability of the N-vinylcarboxylic acid amide is reduced.

The hydrogen partial pressure suitable for the selective hydrogenation reaction of the present invention is from 0.01 to 100 kg/cm$^2$, preferably from 0.5 to 50 kg/cm$^2$. If the hydrogen partial pressure is less than 0.01 kg/cm$^2$, the reaction rate is extremely slow, whereas if it exceeds 100 kg/cm$^2$, the production of N-ethylacetamide resulting from hydrogenation of N-vinylcarboxylic acid amide increases and the equipment becomes more expensive.

When the catalyst is charged and fluidized, the proper conditions of liquid space velocity vary depending upon the hydrogen partial pressure, the reaction temperature and the content of N-1,3-butadinenylcarboxylic acid amide, but the liquid space velocity is preferably from 0.05 to 1000. If it exceeds 1000, the conversion of N-1,3-butadienylcarboxylic acid amide is insufficient, whereas if it is less than 0.05, the reaction efficiency is reduced.

The reaction method for use in the present invention may either be conducted continuously or batchwise, and the reaction vessel is not particularly limited in its structural form. Any of gas-solid contact, gas-liquid-solid contact and solid-liquid contact may be used, however, a solid-liquid reactor capable of uniform contact of the raw material with the catalyst under relatively mild conditions is preferred. When the solid-liquid reaction is conducted, hydrogen is previously dissolved in the crude N-vinylcarboxylic acid amide solution so as to supply the hydrogen necessary for the reaction.

After the hydrogenation reaction, the reaction solution contains a by-product accompanying the product produced by the hydrogenation reaction. Methods for purifying the reaction solution include, for example, rectification, recrystallization by cooling and pressure crystallization of the solution, and these methods may be used individually or in combination. Other than these methods, any method may be used without particular restriction if the by-product and the N-vinylcarboxylic acid amide can be easily separated.

As described above, the N-1,3-butadienylcarboxylic acid amide has a cis form and a trans form and due to difference in the physical properties or reactivity of these, the degree of separation may vary in the present invention.

In that case, a cis-trans isomerization reaction of the N-1,3-butadienylcarboxylic acid amide may be conducted under appropriate reaction conditions in combination with the above-described operations such as separation.

In any case, the N-vinylcarboxylic acid amide causes solvolysis or hydrolysis when an acid is present. Accordingly, it is preferred to place auxiliary facilities for use in the present invention, such as a production apparatus, a separation apparatus, a raw material tank, a product container and a filtrate tank, under an atmosphere of inert gas (nitrogen) or dry air. Furthermore, in order to prevent a hydrolysis reaction of N-vinylcarboxylic acid amide, a slight amount of a drying agent such as magnesium sulfate may be added to the raw material.

When a base is present, a dimerization reaction results. Accordingly, the pH of the N-vinylcarboxylic acid amide solution is preferably adjusted prior to the distillation and adsorption operation to a pH of from 3 to 11, preferably from 4 to 10, more preferably from 5 to 6. When the crude N-vinylcarboxylic acid amide solution is acidic, the pH is adjusted by adding a basic compound. Examples of the basic compound include sodium salts such as sodium carbonate, sodium hydrogencarbonate, sodium hydroxide, sodium (hydrogen)-phosphate and sodium acetate, potassium salts such as potassium carbonate, potassium hydrogencarbonate, potassium hydroxide, potassium (hydrogen)phosphate and potassium acetate, and aromatic amines such as N-phenyl-a-naphthylamine, 4,4'-bis($\alpha,\alpha$-dimethylbenzyl) diphenylamine, N-phenyl-N'-(1,3-dimethylbutyl)-p-phenylenediamine, N-phenyl-N'-isopropyl-p-phenylenediamine, N-phenyl-N'-(1-methylheptyl)-p-phenylenediamine, N-phenyl-N'-cyclohexyl-p-phenylenediamine, N,N'-diphenyl-p-phenylenediamine, N,N'-di-$\beta$-naphthyl-p-phenylenediamine, N,N'-bis(1,4-dimethylpentyl)-p-phenylene-diamine,N,N'-bis(1-ethyl-3-methylpentyl)-p-phenylenediamine, N,N'-bis(1-methylheptyl)-p-phenylenediamine and N-phenyl-N'-(p-toluenesulfonyl)-p-phenylenediamine, with sodium hydroxide being particularly preferred.

The addition amount of the basic compound is preferably from 1 to 10,000 ppm, more preferably from 10 to 1,000 ppm. If the addition amount exceeds 10,000 ppm, in the case of an inorganic salt, the entire amount is not dissolved and no additional effect is expected from the excess amount. In case of an aromatic amine, it is difficult to completely remove the aromatic amine at the purification step, and the polymerizability of N-vinylcarboxylic acid amide is reduced. If the addition amount is less than 1 ppm, almost no stabilizing effect is obtained.

When the crude N-vinylcarboxylic acid amide solution is basic, the adjustment is conducted by adding an acidic compound. Examples of the acidic compound include acidic inorganic compounds such as hydrochloric acid, sulfuric acid, nitric acid, phosphoric acid and a salt thereof, and acidic organic compounds including carboxylic acids such as acetic acid, phthalic acid and citric acid, carbolic acids such as phenol, hydroquinone and catechol, and salts thereof.

Among the methods for use in the present invention, a method for reducing or removing the N-1,3-butadienylcarboxylic acid amide or a precursor thereof contained in the production raw material or intermediate of N-vinylcarboxylic acid amide is described below. The precursor content is expressed in terms of the content of N-1,3-butadienylcarboxylic acid amide when all precursors are converted into N-1,3-butadienylcarboxylic acid amide.

In the process of the present invention, the production raw material or intermediate of N-vinylcarboxylic acid amide includes N-(1-alkoxyethyl)carboxylic acid amide, dialkylacetal and ethylidenebiscarboxylic acid amide. Examples of the alkoxyl group in N-(1-alkoxyethyl)carboxylic acid amide and dialkylacetal include an aliphatic alkoxyl group such as methoxy, ethoxy, n-propyl, isopropoxy, n-butoxy and sec-butoxy. Examples of the carboxylic acid amide group in N-(1-alkoxyethyl)carboxylic acid amide and ethylidenebiscarboxylic acid amide include formamide, N-methylformamide, acetamide, N-methylacetamide, propionamide, butyramide and isobutyramide. Examples of the corresponding compound include: as the N-(1-alkoxyethyl)carboxylic acid amide, N-(1-methoxyethyl) acetamide, N-(1-methoxyethyl)formamide, N-(1-ethoxyethyl)acetamide, N-(1-ethoxyethyl)formamide, N-(1-iso-propoxyethyl)acetamide and N-(1-isopropoxyethyl) formamide; as the dialkylacetal, dimethylacetal, diethylacetal and diisopropylacetal; as the ethylidenebiscarboxylic acid amide, ethylidenebisacetamide, ethylidenebisformamide, ethylidenebis-(N-methylformamide) and ethylidenebispropionamide.

An N-(1-alkoxyethyl)carboxylic acid amide or an ethylidenebiscarboxylic acid amide is converted into an N-vinylcarboxylic acid amide by a known method such as thermal cracking or catalytic cracking. The reaction conditions are, for example, such that a gas phase or a liquid phase is used. The reaction temperature is from 60 to 600° C., the reaction time is from 0.3 second to 2 hours and the reaction pressure is from 0.1 mmHg to atmospheric pressure. Examples of the catalyst used in case of catalytic cracking include an alkali metal salt of carboxylic acid such as potassium acetate and an oxide of an alkali metal or an alkaline earth metal, such as magnesium oxide.

The N-1,3-butadienylcarboxylic acid amide is produced upon elimination of two alcohol molecules induced by the thermal cracking or catalytic cracking of N-(1,3-dialkoxybutyl)carboxylic acid amide, or upon elimination of alcohol and carboxylic acid amide induced by the thermal cracking or catalytic cracking of 3-alkoxybutylidenebiscarboxylic acid amide. The N-(1,3-dialkoxybutyl)carboxylic acid amide and 3-alkoxybutylidenebiscarboxylic acid amide are produced by the reaction of 1,1,3-trialkoxybutane with carboxylic acid amide.

Accordingly, in the present invention, examples of the precursor of N-1,3-butadienylcarboxylic acid amide include 1,1,3-trialkoxybutane, N-(1,3-dialkoxybutyl)carboxylic acid amide and 3-alkoxybutylidenebiscarboxylic acid amide, and examples of the alkoxyl group and the carboxylic acid amide group in these precursors include those described above for the precursor of N-vinylcarboxylic acid amide. Therefore, the 1,1,3-trialkoxybutane includes 1,1,3-trimethoxybutane, 1,1,3-triethoxybutane and 1,1,3-triisopropoxybutane; the N-(1,3-dialkoxybutyl)carboxylic acid amide includes N-(1,3-dimethoxybutyl)acetamide, N-(1,3-dimethoxybutyl)formamide, N-(1,3-diethoxybutyl)acetamide, N-(1,3-diethoxybutyl)-formamide, N-(1,3-diisopropoxybutyl)acetamide and N-(1,3-diisopropoxybutyl)formamide; and the 3-alkoxybutylidenebiscarboxylic acid amide includes 3-methoxybutylidenebisacetamide, 3-methoxybutylidenebisformamide, 3-ethoxybutylidenebisacetamide, 3-ethoxybutylidenebisformamide, 3-isopropoxybutylidenebisacetamide and 3-isopropoxybutylidenebisformamide.

The embodiment for reducing the content of N-1,3-butadienylcarboxylic acid amide or a precursor thereof in the production raw material or intermediate of N-vinylcarboxylic acid amide to 30 ppm or less includes, for example, a rectification method, a recrystallization method by cooling the precursor solution of N-vinylcarboxylic acid amide, a pressure crystallization method of the precursor, a physical adsorption method by treating the precursor with an adsorbent such as activated carbon and a method of chemically processing the precursor, and these methods may be used individually or in combination. Other methods may be used without particular limitation as long as the N-1,3-butadienylcarboxylic acid amide or a precursor thereof can be easily separated from the production raw material or intermediate of the N-vinylcarboxylic acid amide.

Furthermore, as a result of extensive investigations on the process for producing an N-vinylcarboxylic acid amide having good polymerizability, the present inventors have found that an N-vinylcarboxylic acid amide for use in the synthesis of a high molecular weight polymer is produced when, in producing an N-vinylcarboxylic acid amide by thermal cracking or catalytic cracking of N-(1-alkoxyethyl) carboxylic acid amide or ethylidenebiscarboxylic acid amide, the N-vinylcarboxylic acid amide content of the N-(1-alkoxyethyl)-carboxylic acid amide or ethylidenebiscarboxylic acid amide is reduced to 10 wt % or less and the pH of a 33 wt % aqueous solution (hereinafter simply referred to as "pH") of the N-(1-alkoxyethyl)carboxylic acid amide or ethylenebiscarboxylic acid amide is adjusted to from 5 to 10.

More specifically, the present invention provides a process for producing an N-vinylcarboxylic acid amide having good polymerizability, wherein, when an N-vinylcarboxylic acid amide is produced by thermal cracking or catalytic cracking of N-(1-alkoxyethyl)carboxylic acid amide or ethylidenebiscarboxylic acid amide, the N-vinylcarboxylic acid amide content of the N-(1-alkoxyethyl)carboxylic acid amide or ethylenebiscarboxylic acid amide is reduced to 10 wt % or less, preferably S wt % or less, more preferably 3 wt % or less, the pH of the N-(1-alkoxyethyl)carboxylic acid amide or ethylidenebiscarboxylic acid amide is adjusted to from 5 to 10, preferably from 6 to 8, more preferably from 6.3 to 7.5, and still more preferably, the N-vinylcarboxylic acid amide content is reduced to 3 wt % or less and at the same time, the pH is adjusted to from 6.3 to 7.5.

There are various reasons why the N-(1-alkoxyethyl) carboxylic acid amide or ethylidenebiscarboxylic acid amide generally contains more than 10 wt % of N-vinylcarboxylic acid amide.

One reason is that when a reaction solution containing N-(1-alkoxyethyl)carboxylic acid amide or ethylidenebiscarboxylic acid amide obtained by the above-described synthesis method is purified and separated by a distillation operation or the like, a part of the N-(1-alkoxyethyl) carboxylic acid or ethylidenebiscarboxylic acid amide is cracked into N-vinylcarboxylic acid amide.

Another reason is that when an N-vinylcarboxylic acid amide is synthesized by thermal cracking or catalytic cracking of N-(1-alkoxylethyl)carboxylic acid amide or ethylidenebiscarboxylic acid amide and the N-vinylcarboxylic acid is separated, the unreacted N-(1-alkoxylethyl) carboxylic acid amide or ethylidenebiscarboxylic acid amide which contains N-vinylcarboxylic acid is recycled for cracking.

A method for reducing the N-vinylcarboxylic acid amide content of N-(1-alkoxyethyl)carboxylic acid amide or ethylidenebiscarboxylic acid amide to 10 wt % or less is described below.

The method is not particularly limited as long as it is a method for reducing the N-vinylcarboxylic acid amide content of N-(1-alkoxyethyl)carboxylic acid amide or ethylidenebiscarboxylic acid amide to 10 wt % or less. The method includes, for example, the processing of N-(1-alkoxyethyl)carboxylic acid amide, ethylidenebiscarboxylic acid amide or a solution of these by a rectification method, an azeotropic distillation method, a recrystallization method or a pressure crystallization method, and these methods may be used individually or in combination. Other than these methods, any method may be used without any particular restriction if it is a method where N-(1-alkoxyethyl)-carboxylic acid amide or ethylidenebiscarboxylic acid amide and N-vinylcarboxylic acid amide can be easily separated.

The embodiment for reducing the N-vinylcarboxylic acid amide content of N-(1-alkoxyethyl)carboxylic acid amide or ethylidenebiscarboxylic acid amide to 10 wt % or less is described in greater detail below.

In the process of the present invention, the distillation apparatus used for separating by a rectification method is not particularly limited and a plate column or packed column having a theoretical plate number of from 1 to 50 may be used, but it is preferable to use a rectification column which causes little pressure loss and has excellent rectification capabilities. An example of such a rectification column is a packed column using a regular filling. N-(1-alkoxyethyl) carboxylic acid amide, ethylidenebiscarboxylic acid amide and N-vinylcarboxylic acid amide are readily deteriorated due to heat. Thus, it is preferable to effect distillation at as low a temperature as possible. Accordingly, the distillation is conducted under a reduced pressure of from 0.01 to 100 mmHg.

The present invention may be conducted either continuously or batchwise, however, in view of productivity and operation safety, a continuous operation is preferred. The reflux ratio is not particularly limited and can be set according to the content and kind of N-vinylcarboxylic acid amide and the capabilities of the distillation column. However, the ref lux ratio is generally from 0.1 to 20, and preferably from 0.5 to 10.

In the process of the present invention, when the separation is effected according to a recrystallization method by cooling the N-(1-alkoxyethyl)carboxylic acid amide or ethylidenebiscarboxylic acid amide solution, the recrystallization solvent, apparatus and process described above with respect to the recrystallization method for N-vinylcarboxylic acid amide can be used.

A method for adjusting the pH of N-(1-alkoxyethyl)-carboxylic acid amide or ethylidenebiscarboxylic acid amide to from 5 to 10 is described below.

The pH of N-(1-alkoxyethyl)carboxylic acid amide or ethylidenebiscarboxylic acid amide becomes less than 5 due to the presence of a carboxylic acid such as acetic acid therein. Although it is not clearly known why the carboxylic acid is mixed therein, it is considered that this results from oxidation of acetaldehyde used in the synthesis of N-(1-alkoxyethyl)carboxylic acid amide or ethylidenebiscarboxylic acid amide, or the production of carboxylic acid amide by solvolysis.

The method for adjusting the pH of N-(1-alkoxyethyl) carboxylic acid amide or ethylidenebiscarboxylic acid amide to from 5 to 10, is not particularly limited. The method includes, for example, the processing of N-(1-alkoxyethyl)carboxylic acid amide, ethylidenebiscarboxylic acid amide or a solution of these by a rectification method, an azeotropic distillation method, a recrystallization method, a pressure crystallization method, a physical method using treatment with an adsorbent or a chemical method using neutralization by an acid or a base, and these methods may be used either individually or in combination.

Among these methods, the physical method including processing by a rectification method, an azeotropic distillation method, a recrystallization method or a pressure crystallization method may be made in the same manner as described above with respect to the removal of N-vinylcarboxylic acid amide. The method using an adsorbent includes a method where an anion exchange resin is used as an adsorbent.

Examples of the basic compound for use in neutralizing an acid as a chemical method include a sodium salt such as sodium carbonate, sodium hydrogencarbonate, sodium hydroxide, sodium (hydrogen)phosphate and sodium acetate, and a potassium salt such as potassium carbonate, potassium hydrogencarbonate, potassium hydroxide, potassium (hydrogen)phosphate and potassium acetate.

When the N-(1-alkoxyethyl)carboxylic acid amide or ethylidenebiscarboxylic acid amide solution is basic, the pH thereof is adjusted by adding an acidic compound. Examples of the acidic compound include acidic inorganic compounds such as hydrochloric acid, sulfuric acid, nitric acid, phosphoric acid and a salt thereof, and acidic organic compounds including carboxylic acids such as acetic acid, phthalic acid and citric acid, carbolic acids such as phenol, hydroquinone and catechol, and salts thereof.

The conversion of N-(1-alkoxyethyl)carboxylic acid amide or ethylidenebiscarboxylic acid amide into N-vinylcarboxylic acid amide is effected by the above-described thermal cracking or catalytic cracking.

In the present invention, the N-(1-alkoxyethyl)carboxylic acid amide or ethylidenebiscarboxylic acid amide causes solvolysis or hydrolysis when an acid is present. Accordingly, it is preferred to install auxiliary facilities for use in the present invention, such as a production apparatus, a separation apparatus, a raw material tank, a product container and a filtrate tank, in an atmosphere of inert gas (nitrogen) or dry air. Furthermore, in order to prevent a hydrolysis reaction of N-(1-alkoxyethyl)carboxylic acid amide or ethylidenebiscarboxylic acid amide, a slight amount of a drying agent such as magnesium sulfate may be added to the raw material.

In the present invention, when an N-vinylcarboxylic acid amide is produced by thermal cracking or catalytic cracking of N-(1-alkoxyethyl)carboxylic acid amide or ethylidenebiscarboxylic acid amide, the N-vinylcarboxylic acid amide content of the N-(1-alkoxyethyl)carboxylic acid amide or ethylidenebiscarboxylic acid amide is reduced to 10 wt % or less, preferably 5 wt % or less, more preferably 3 wt % or less, the pH of the N-(1-alkoxyethyl)carboxylic acid amide or ethylidenebiscarboxylic acid amide is adjusted to from 5 to 10, preferably from 6 to 8, more preferably from 6.3 to 7.5, and still more preferably, the N-vinylcarboxylic acid amide content is reduced to 3 wt % or less and at the same time, the pH is adjusted to from 6.3 to 7.5, whereby an N-vinylcarboxylic acid amide having the desired polymerizability is obtained. If the N-vinylcarboxylic acid amide content exceeds the above described range, it tends to be difficult to obtain a highly polymerizable N-vinylcarboxylic acid amide by thermal cracking or catalytic cracking of N-(1-alkoxyethyl)carboxylic acid amide or ethylidenebiscarboxylic acid amide. Also, if the pH exceeds the above-described range, it tends to be difficult to obtain a highly polymerizable N-vinylcarboxylic acid amide by thermal cracking or catalytic cracking of N-(1-alkoxyethyl) carboxylic acid amide or ethylidenebiscarboxylic acid amide.

The present invention provides a process for producing a homopolymer or copolymer of N-vinylcarboxylic acid amide using the above-described N-vinylcarboxylic acid amide.

By using a highly polymerizable N-vinylcarboxylic acid amide in which the crude N-vinylcarboxylic acid amide has an N-1,3-butadienylcarboxylic acid amide content of 30 ppm or less, a homopolymer of a high molecular weight N-vinylcarboxylic acid amide or a copolymer thereof with other copolymerizable monomer can be obtained.

As used herein, "highly polymerizable" means that the viscosity as measured following the procedure of Example 1 is 30 cps or more, preferably 60 cps or more, and also means that the peak achieving time as measured following the procedure of Example 13 is 15 hours or less, preferably 10 hours or less. The term "high molecular weight" means a weight average molecular weight of 500,000 or more, preferably 1,000,000 or more.

Specific examples of representative monomers copolymerizable with the N-vinylcarboxylic acid amide of the present invention include:

an alkali metal salt such as a sodium salt or potassium salt of acrylic acid or methacrylic acid; an alkyl ester of the alkali metal salt, such as methyl ester, ethyl ester, propyl ester, butyl ester, pentyl ester, hexyl ester, heptyl ester, octyl ester, nonyl ester, decyl ester, stearyl ester and palmityl ester; a hydroxy lower alkyl ester of the alkali metal salt, such as hydroxyethyl ester, hydroxypropyl ester and hydroxybutyl ester; a lower alkyl ester substituted by a lower alkylamino group of the alkali metal salt, such as dimethylaminomethyl ester, dimethylaminoethyl ester, dimethylaminopropyl ester, dimethylaminobutyl ester, diethylaminomethyl ester, diethylaminoethyl ester, diethylaminopropyl ester and diethylaminobutyl ester; a lower alkyl ester halide (the halide being preferably chloride or bromide) substituted by a quaternary ammonium group of the alkali metal salt, such as trimethylammonioethyl ester halide, trimethylammoniopropyl ester halide, triethylammonioethyl ester halide and triethylammoniopropyl ester halide; an amide of the alkali metal salt; an amide substituted by a lower alkylamino group of the alkali metal salt, such as dimethylaminomethylamide, dimethylaminoethylamide, dimethylaminoproylamide, dimethylaminobutylamide, diethylaminomethylamide, diethylaminoethylamide, diethylaminopropylamide and diethylaminobutylamide; a lower alkylamide substituted by a quaternary ammonium group of the alkali metal salt, such as trimethylammonioethylamide halide, triethylammoniopropylamide halide, triethylammonioethylamide halide and triethylammoniopropylamide halide; a lower alkylamide substituted by a sulfonic acid or an alkali metal sulfonic acid of the alkali metal salt, such as sulfomethylamide, sulfoethylamide, sulfopropylamide, sulfobutylamide, sodium sulfomethylamide, sodium sulfoethylamide, potassium sulfopropylamide, potassium sulfobutylamide, potassium sulforethylamide, potassium sulfoethylamide, potassium sulfopropylamide and potassium sulfobutylamide; an acrylonitrile; a vinyl ether such as methyl vinyl ether, ethyl vinyl ether, propyl vinyl ether and a butyl vinyl ether; a vinyl ketone such as methyl vinyl ketone and ethyl vinyl ketone; a lower vinyl carboxylate such as vinyl acetate and vinyl propionate; a maleic anhydride; a maleic acid; sodium maleate; and potassium maleate.

Among these preferred are (meth)acrylic acid , sodium (meth) acrylate, methyl (meth) acrylate, ethyl (meth) acrylate, propyl (meth)acrylate , butyl (meth)acrylate, 2-hydroxyethyl (meth)acrylate, 2-hydroxypropyl (meth) acrylate, 2-hydroxybutyl (meth)acryl (methacrylatminoethyl (meth)acrylate, trimethylaminoethyl (meth)acrylate chloride, acrylamide, sodium sulfopropylacrylamide, sodium sulfobutylacrylamide, acrylonitrile, methyl vinyl ether, ethyl vinyl ether, methyl vinyl ketone, ethyl vinyl ketone, vinyl acetate, N-vinyl-2-pyrrolidone and maleic anhydride. As used herein, "(meth) acrylic acid" means acrylic acid or methacrylic acid.

In the present invention, a crosslinking monomer or crosslinking agent which is a compound having two or more unsaturated groups in one molecule, may be used as a monomer copolymerizable with N-vinylcarboxylic acid amide.

The polymerization process is not necessarily limited and conventionally known processes may be used. Usually, a solution polymerization process, a reverse-phase suspension polymerization process or a reverse-phase emulsion polymerization process is preferably used.

For example, in the solution polymerization process, monomer components and a crosslinking agent are uniformly dissolved in water, an organic solvent or a mixed solvent of these, the dissolved oxygen in the system is removed by vacuum deaeration or displacement by an inactive gas such as nitrogen or carbon dioxide gas and then, a polymerization initiator is added to the system to start the reaction. The polymerization initiation temperature is usually approximately from −10 to 60° C. and the reaction time is approximately from 1 to 10 hours.

The N-1,3-butadienylcarboxylic acid amide of the present invention is verified and identified by mass spectra (an electron impact method and a chemical ionization method), an infrared light absorption spectrum and an ultraviolet light absorption spectrum. For example, N-1,3-butadienylacetamide is identified as follows.

Physical properties of N-1,3-butadienylacetamide:
Mass spectrum (electron impact method): 111, 69, 54, 43
Mass spectrum (chemical ionization method): 112
Infrared light absorption spectrum ($cm^{-1}$):
3099, 1732, 1654, 1471
Ultraviolet light absorption spectrum (nm): 237, 276

In the present invention, the quantitative analysis of N-1,3-butadienylcarboxylic acid amide is preferably made by high-speed liquid column chromatography, but the present invention not limited to this method. For example, the following operating conditions of a high-speed liquid column chromatography are preferred. Unless otherwise indicated, the quantitative analysis was conducted under these conditions in the Examples of the present invention.

Column: SHODEX® SIL5B (Showa Denko K.K.)
Eluate: n-Hexane/isopropyl alcohol (9/1), 1 mL/min
Detector: Ultraviolet detector, 254 nm The present invention will be described below in greater detail by referring to the following Examples and Comparative Examples, however, the present invention should not be construed as being limited thereto.

EXAMPLE 1

To a three-necked flask (200 ml) with a thermometer and a dry ice-ethanol trap, 5.9 g (0.1 mol) of acetamide, 40 g (0.67 mol) of isopropyl alcohol, 2.16 g (15 mmol) of ethylidenebisacetamide and 14.6 g (0.1 mol) of acetaldehyde diisopropylacetal were added, and the mixture was stirred and dissolved at a temperature of from 45 to 48° C. until it became uniform. A solution containing 0.43 g (0.1 wt % based on the charge) of concentrated sulfuric acid dissolved in 2 g (33 mmol) of isopropyl alcohol (the same in the following examples) was added and after stirring, 17.6 g (0.4 mol) of acetaldehyde was added thereto through a dropping funnel over a period of 3 minutes. After the dropping addition, the mixture was allowed to react at 50° C. for 3 hours to neutralize the catalyst. The reaction mixture was then analyzed by gas chromatography to find that the acetamide conversion was 88%, the selectivity of N-(1-propoxyethyl)acetamide was 94% and the selectivity of ethylidenebisacetamide as a by-product was 5.3%. From the resulting reaction solution, N-(1-propoxyethyl)acetamide was obtained by distillation under reduced pressure and thermally cracked into N-vinylacetamide and isopropyl alcohol at 450° C. and a residence time of 1 second. The cracked solution was cooled to 20° C. and the mother solution was separated therefrom at 1800 kg/cm² and 20° C. in a high-pressure crystallizer. As a result, N-vinylacetamide in a purity of 99.9% and having an N-1,3-butadienyl content of 1 ppm was obtained. In order to evaluate the polymerizability of the N-vinylacetamide, distillated water was added thereto to give a concentration of 17 wt % and after displacement by nitrogen, 500 ppm of V-50 (N,N'-azobis- (2-amidinopropane) dihydrochloride was added thereto and the container was dipped in a constant-temperature water bath of 45° C. After 10 minutes, the system was diluted by 9 wt % of a 1% aqueous solution of hydroquinone and the viscosity was measured at 30° C. and a revolution number of 30 rpm using a BL-type (rotary) viscometer and found to be 130 cps.

COMPARATIVE EXAMPLE 1

The thermally cracked solution obtained in Example 1 was subjected to simple distillation at a pressure of 0.5 mmHg to provide N-vinylacetamide in a purity of 97.5% and having an N-1,3-butadienylacetamide content of 200 ppm. The polymerizability evaluation was conducted in the same manner as in Example 1, and the viscosity was found to be 10 cps or less.

EXAMPLE 2

Synthesis of acetal:

Into the fifth stage from the top of a glass-made Oldershaw-type rectification column having 25 stages, methanol containing 0.5 wt % of sulfuric acid was introduced in an amount of 180 g per hour and into the fifteenth stage from the top, acetaldehyde was introduced in an amount of 27 g per hour. At the bottom of the rectification column, a 500 ml-volume flask having placed therein 100 g of water was provided and heated at 100° C. to extract the content of the flask in an amount of 29 g per hour. The solution extracted from the flask contained substantially no organic matter. From the top of column, 221 g/h of a dimethylacetal-methanol mixture was extracted at a reflux ratio of 2. The distillate contained substantially no water and aldehyde. The acetaldehyde conversion was 100% and the yield of dimethylacetal was 100%.

Separation of acetal:

Into the first stage from the top of a glass-made Oldershaw-type rectification column having 25 stages, n-hexane was introduced in an amount of 56 g per hour and into the tenth stage from the top, dimethylacetal containing 28 wt % of methanol was introduced in an amount of 71 g per hour. The column was heated so that the temperature of the column top was maintained at 50° C. at a reflux ratio of 6. At the lower part of the rectification column, a 500 ml-volume flask having placed therein 100 g of dimethylacetal was provided and heated by dipping it in an oil bath at 110° C. to thereby extract the content of the flask in an amount of 47 g per hour. The solution extracted from the flask was dimethylacetal substantially free of n-hexane and containing 0.3% of methanol. From the top of column, 80 g/h of a dimethylacetal-methanol-n-hexane mixture was extracted. The distillate and the bottom product each contained substantially no water or acetaldehyde.

Synthesis of N-(1-methoxyethyl)acetamide:

The high-purity dimethylacetal obtained in the acetal separation process and the dimethylacetal containing methanol obtained in the methanol recovery process were mixed, and dry acetamide was dissolved therein to prepare a reaction raw material solution of acetamide/dimethylacetal/methanol at a molar ratio of 1/20/3. This solution was introduced from the lower part of a reaction tube having an inner diameter of 40 mm charged with 60 ml of a strongly acidic ion exchange resin Amberlist 15, in an amount of 5 ml per hour. Into the jacket of the reaction tube, hot water at 55° C. was circulated to control the reaction temperature to 55° C. The reaction solution obtained from the exit at the upper portion of the reaction vessel was subjected to quantitative analysis and, as a result, it was found that the reaction solution had a molar composition comprising approximately acetamide/dimethyl-acetal/methanol/MEA of 0/19/4/0.9, the acetamide conversion was 98% and the yield of N-(1-methoxyethyl)acetamide (MEA) was 90%.

Recovery of acetal:

The reaction solution obtained in the synthesis step of N-(1-methoxyethyl)acetamide was fed to a thin film-type continuous flash evaporator with a jacket having a heating area of 0.04 m$^2$ under a reduced pressure of 100 mmHg, in an amount of 600 g per hour. In the jacket, a heating medium was circulated. A residue on evaporation substantially comprising N-(1-methoxyethyl)acetamide was obtained in an amount of 17 g per hour. A solution comprising dimethylacetal containing 7 wt % of methanol with the volatile components being condensed was obtained in an amount of 583 g per hour.

Recovery of methanol:

Into the tenth stage from the top of a glass-made Oldershaw-type rectification column having 25 stages, the dimethylacetal fraction of distillate containing 7 wt % of methanol obtained in the acetal recovery step was introduced in an amount of 200 g per hour. The column was heated so that the temperature of the column top was maintained at 58° C. at a reflux ratio of 6. At the lower potion of the rectification column, a 500 ml-volume flask was provided and heated by dipping it in an oil bath at 110° C. to extract the content of the flask in an amount of 185 g per hour. The solution extracted from the flask was dimethylacetal containing 5.6 wt % of methanol. From the column top, a dimethylacetal-methanol azeotropic mixture (methanol: 24 wt %) was extracted in an amount of 15 g per hour.

Synthesis of N-vinylacetamide:

The solution substantially comprising N-(1-methoxyethyl)acetamide obtained in the acetal recovery step was fed into a stainless steel reaction tube having an inner diameter of 20 mm and a total length of 6 m, which was under a reduced pressure of 100 mmHg and heated at 450° C., in an amount of 20 ml per minute. The mixture of N-vinylacetamide and methanol -produced by the thermal cracking reaction was condensed in a condenser provided at the exit of the reaction tube and recovered. The conversion of N-(1-methoxyethyl)-acetamide was 92%.

Concentration of N-vinylacetamide:

Into the tenth stage from the top of a glass-made Oldershaw-type rectification column having 10 stages, the reaction solution obtained in the synthesis step of N-vinylacetamide was introduced in an amount of 200 g per hour. The pressure was 200 mmHg and the column was heated so that the temperature of the column top was maintained at 40° C. at a reflux ratio of 2. A 500 ml-volume flask was provided at the lower portion of the rectification column and heated by dipping in an oil bath at 80° C. to extract the content of the flask in an amount of 155 g per hour. The solution extracted from the flask was a crude N-vinylacetamide solution containing 94 wt % of N-vinylacetamide. From the column top, methanol was extracted in an amount of 45 g per hour. The crude N-vinylacetamide contained 70 ppm of N-1,3-butadienylacetamide.

Purification of N-vinylacetamide:

The crude N-vinylacetamide solution obtained in the concentration step of N-vinylacetamide was introduced into the fifth stage from the top of a glass-made oldershaw-type rectification column having 10 stages and rectification was conducted under a reduced pressure of 0.15 mmHg and at a reflux ratio of 3. As a result, N-vinylacetamide in a purity of 98% and containing 4 ppm of N-1,3-butadienylacetamide was obtained. The polymerizability of the resulting N-vinylacetamide was evaluated in the same manner as in Example 1, and the viscosity was found to be 100 cps.

EXAMPLE 3

The crude N-vinylacetamide containing 70 ppm of N-1,3-butadienylacetamide obtained in the concentration step of N-vinylacetamide in Example 2 was adjusted to 50° C. and the mother solution was separated therefrom at 1,800 kg/cm$^2$ and 50° C. in a high-pressure crystallizer. As a result, N-vinylacetamide in a purity of 99.9% and having an N-1,3-butadienylacetamide content of 1 ppm or less was obtained. The polymerizability of the resulting N-vinylacetamide was evaluated in the same manner as in Example 1, and the viscosity was found to be 150 cps.

EXAMPLE 4

The methanol solution of N-vinylacetamide containing 70 ppm of N-1,3-butadienylacetamide obtained in the synthesis step of N-vinylacetamide in Example 2 was introduced into a column charged with activated carbon at a LHSV of 2 Hr$^{-1}$ and room temperature. The resulting solution contained 9 ppm of N-1,3-butdienylacetamide. The resulting solution was subjected to simple distillation under reduced pressure. The polymerizability of the distilled N-vinylacetamide was evaluated in the same manner as in Example 1, and the viscosity was found to be 70 cps.

EXAMPLE 5

To 50 parts by weight of N-vinylacetamide containing 200 ppm of N-1,3-butadienylacetamide obtained in Comparative Example 1, 50 parts by weight of toluene was added and dissolved at 40° C. in a nitrogen atmosphere. After cooling the mixture to 4° C., the precipitated crystals were separated by filtration and dried under reduced pressure. The resulting N-vinylacetamide contained 8 ppm of N-1,3-butadienylacetamide. The polymerizability of this product was evaluated in the same manner as in Example 1, and the viscosity was found to be 80 cps.

EXAMPLE 6

To the methanol solution of N-vinylacetamide containing 70 ppm of N-1,3-butadienylacetamide obtained in the synthesis step of N-vinylacetamide in Example 2, p-benzoquinone was added to give a concentration of 97 ppm (1.5 equivalent to the N-1,3-butadienylacetamide) and stirred at room temperature for 1 hour. The reaction solution contained 9 ppm of N-1,3-butadienylacetamide. The solution was subjected to simple distillation under reduced pressure. The polymerizability of the distilled N-vinylacetamide was evaluated in the same manner as in Example 1, and the viscosity was found to be 70 cps.

EXAMPLE 7

Five grams of solid catalyst comprising 0.5 wt % of palladium carried on an alumina carrier and 50 g of crude N-vinylacetamide containing 70 ppm of N-1,3-butadienylacetamide, 55 wt % of N-vinylacetamide, 15 wt % of N-(1-methoxyethyl)-acetamide, 7 wt % of acetamide and 20 wt % of methanol were placed in a 200 ml-volume flask and reacted in a hydrogen atmosphere at room temperature for 30 minutes while stirring. After completion of the reaction, the catalyst was separated by filtration from the reaction solution and the filtrate was analyzed. The N-1,3-butadienylacetamide was analyzed by HPLC and other components were analyzed by gas chromatography. The reaction solution had an N-1,3-butadienylacetamide content of 1 ppm or less and contained 0.4 wt % of N-ethylacetamide.

After removing methanol by distillation under reduced pressure, N-vinylacetamide was crystallized in a high-pressure crystallizer under a pressure of 2,000 kg/cm and the mother solution was separated at 40° C. The resulting N-vinylacetamide had a purity. of 99.3 wt % and an N-1,3-butadienylacetamide content of 1 ppm or less. The polymerizability was evaluated in the same manner as in Example 1, and the viscosity was found to be 160 cps.

EXAMPLE 8

A solid catalyst (2.5 g) comprising 0.5 wt % of palladium carried on an alumina carrier was charged into a hydrogenation reactor in a nitrogen atmosphere. Under the nitrogen atmosphere, 95 kg of crude N-vinylacetamide containing 400 ppm of N-1,3-butadienylacetamide, 55 wt % of N-vinylacetamide, 15 wt % of N-(1-methoxyethyl) acetamide and 20 wt % of methanol was circulated in the reaction vessel at a liquid space velocity (LHSV) of 60 Hr$^{-1}$ for 6 hours. The reaction solution had an N-1,3-butadienylacetamide content of 1 ppm or less and contained 0.3 wt % of N-ethylacetamide.

After removing methanol by distillation under reduced pressure from the resulting reaction solution, the mother solution was separated in a high-pressure crystallizer at 1,800 kg/cm$^2$ and 30° C. As a result, N-vinylacetamide in a purity of 99.5 wt % and having an N-1,3-butadienylacetamide content of 1 ppm or less was obtained.

The polymerizability of the resulting N-vinylacetamide was evaluated in the same manner as in Example 1, and the viscosity was found to be 170 cps.

EXAMPLE 9

A solid catalyst (25 g) comprising 0.5 wt % of palladium carried on an alumina carrier was charged in a hydrogenation reaction vessel in a nitrogen atmosphere and crude N-vinylacetamide containing 400 ppm of N-1,3-butadienylacetamide, 55 wt % of N-vinylacetamide, 15 wt % of N-(1-methoxyethyl)acetamide, 7 wt % of acetamide and 20 wt % of methanol was circulated therein. The reaction solution had an N-1,3-butadienylacetamide content of 1 ppm or less and contained 0.5 wt % of N-ethylacetamide.

After removing methanol from the resulting reaction solution, the mother solution was separated in a high-pressure crystallizer at 1,800 kg/cm$^2$ and 30° C. As a result, N-vinylacetamide in a purity of 99.5 wt % and having an N-1,3-butadienylacetamide content of 1 ppm or less was obtained.

The polymerizability of the resulting N-vinylacetamide was evaluated in the same manner as in Example 1, and the viscosity was found to be 170 cps.

EXAMPLE 10

This experiment was conducted in the same manner as in Example 7, except that a catalyst comprising 0.05 wt % of palladium and 0.3 wt % of silver carried on an alumina carrier was used in place of the catalyst comprising 0.5 wt % of palladium carried on an alumina carrier, and the reaction time was changed to 1 hour. The reaction solution had an N-1,3-butadienylacetamide content of 1 ppm or less and contained 0.4 wt % of N-ethylacetamide. The polymerizability of the resulting N-vinylacetamide was evaluated in the same manner as in Example 1, and the viscosity was found to be 170 cps.

EXAMPLE 11

The dimethylacetal containing 7 wt % of methanol obtained in the acetal recovery step in Example 2 was returned to the acetal separation step and methanol was separated from acetal. The resulting acetal contained 250 ppm of 1,1,3-trimethoxybutane. This acetal was distilled using a packed column having a theoretical plate number of 20 at a ref lux ratio of 5 to obtain acetal containing 12 ppm of 1,1,3-trimethoxybutane. The resulting acetal was subjected to the processes subsequent to the synthesis step of 1-methoxyethylacetamide as described in Example 3. However, in this example, simple distillation was conducted in place of rectification at the N-vinylacetalamide purification step. The resulting N-vinylacetamide contained 10 ppm of N-1,3-butadienylacetamide. The polymerizability of the resulting product was evaluated in the same manner as in Example 1, and the viscosity was found to be 70 cps.

COMPARATIVE EXAMPLE 2

N-vinylacetamide was produced in the same manner as in Example 1 except for omitting the rectification of acetal. The resulting N-vinylacetamide contained 230 ppm of N-1,3-butadienylacetamide. The polymerizability was evaluated in the same manner as in Example 1, and the viscosity was found to be 10 cps or less.

EXAMPLE 12

The residue on evaporation substantially comprising N-(1-methoxyethyl)acetamide obtained in the acetal recovery step in Example 2 was distilled using a packed column having a theoretical-plate number of 20 at a reflux ratio of 6 to obtain N-(1-methoxyethyl)acetamide containing 11 ppm of N-(1,3-dimethoxybutyl)acetamide. The resulting N-(1-methoxyethyl)acetamide was subjected to the synthesis step of N-vinylacetamide as described in Example 3, except that simple distillation was conducted in place of rectification at the N-vinylacetamide purification step. The resulting N-vinylacetamide contained 9 ppm of N-1,3-butadienylacetamide. The polymerizability was evaluated in the same manner as in Example 1, and the viscosity was found to be 80 cps.

COMPARATIVE EXAMPLE 3

N-vinylacetamide was produced in the same manner as in Example 9, except for omitting rectification of N-(1-methylethyl)acetamide. The resulting N-vinylacetamide contained 230 ppm of N-1,3-butadienylacetamide. The polymerizability was evaluated in the same manner as in Example 1, and the viscosity was found to be 10 cps or less.

EXAMPLE 13

To a glass-made reaction vessel, 745 g of water, 250 g of N-vinylacetamide obtained in Example 2 and 0.409 g of N,N'-(diacetyl)-N,N'-(divinyl)-1,4-bis(aminomethyl) cyclohexane as a crosslinking agent were added and dissolved. After removing the dissolved oxygen by a nitrogen gas, 0.075 g of 2,2'-azobis 2-(2-imidazolin-2-yl)propane dihydrochloride dissolved in 5 ml of deaerated water was added, and the mixture was insulated from heat and allowed to stand. After 7 hours, the inner temperature of the reaction vessel reached 71° C. due to polymerization heat and thereafter, the inner temperature gradually lowered due to heat loss. The time period from the addition of a polymerization initiator to the time when the inner temperature of the reaction vessel reaches a maximum is called the "peak achieving time". In this example, the peak achieving time was 7 hours.

COMPARATIVE EXAMPLE 4

The polymerization was conducted in the same manner as in Example 13, except that N-vinylacetamide obtained in Comparative Example 1 was used in place of N-vinylacetamide obtained in Example 2. An increase of inner temperature accompanying the polymerization was not observed even after 48 hours from the addition of the polymerization initiator.

EXAMPLE 14

To a glass-made reaction vessel, 745 g of water, 225 g of N-vinylacetamide obtained in Example 2 and 27.6 g of sodium acrylate were added and dissolved. After removing the dissolved oxygen by a nitrogen gas, 0.075 g of 2,2'-azobis 2-(2-imidazolin-2-yl)propane dihydrochloride dissolved in 5 ml of deaerated water was added, and the mixture was isolated from heat and allowed to stand. The peak achieving time was 6 hours.

COMPARATIVE EXAMPLE 5

The polymerization was conducted in the same manner as in Example 13, except that N-vinylacetamide was used in place of N-vinylacetamide obtained in Example 2. An increase of inner temperature accompanying the polymerization was not observed even after 48 hours from the addition of the polymerization initiator.

EXAMPLE 15

A solution having a pH of 6.5 (determined with a 33 wt % aqueous solution) and containing 98 wt % of N-(1-methoxyethyl)acetamide and 2 wt % of acetamide was fed in an amount of 35 g per minute into a stainless steel reaction tube having an inner diameter of 21 mm and a total length of 6 m. The reaction tube was heated to 400° C., and the pressure was reduced to 100 mmHg. A mixture of N-vinylacetamide and methanol produced by the thermal cracking reaction was condensed in a condenser provided at the exit of the reaction tube and recovered. The N-vinylacetamide contained 28 ppm of N-1,3-butadienylacetamide, and the conversion of N-(1-methoxyethyl)acetamide was 85%.

The resulting reaction solution was introduced into the tenth stage from the top of a glass-made oldershaw-type rectification column having 10 stages, in an amount of 200 g per hour. The column was heated so that the temperature of the column top was maintained at 40° C. at a reduced pressure of 200 mH and a reflux ratio of 2. A 500 ml-volume flask was provided at the lower portion of the rectification column and heated by dipping in an oil bath of 80° C. to extract the content of the flask in an amount of 155 g per hours. The solution extracted from the flask was a crude N-vinylacetamide solution containing 94 wt % of N-vinylacetamide. From the top of column, methanol was extracted in an amount of 45 g per hour.

The resulting crude N-vinylacetamide solution was introduced into the fifth stage from the top of a glass-made Oldershaw-type rectification column having 10 stages and subjected to rectification in a reduced pressure of 0.15 mmHg and at a reflux ratio of 3. As a result, N-vinylacetamide in a purity of 98% and having an N-1,3-butadienylacetamide content of 0.9 ppm was obtained. The polymerizability of the resulting N-vinylacetamide was evaluated in the same manner as in Example 1, and the viscosity was found to be 100 cps.

REFERENCE EXAMPLE 1

From the methanol solution of N-vinylacetamide containing 28 ppm of N-1,3-butadienylacetamide obtained in Example 15, the methanol was removed by distillation. After concentrating the N-vinylacetamide, the temperature was adjusted to 50° C. and the mother solution was separated in a high-pressure crystallizer at 1,800 kg/cm$^2$ and 50° C. As a result, N-vinylacetamide in a purity of 99.9% and containing 2 ppm of N-1,3-butadienylacetamide was obtained. The polymerizability of the resulting N-vinylacetamide was evaluated in the same manner as in Example 1, and the viscosity was found to be 80 cps.

EXAMPLES 16 TO 19 AND COMPARATIVE EXAMPLES 6 TO 9

A reaction was conducted in the same manner as in Example 15, except for using N-(1-methoxyethyl)acetamide containing N-vinylacetamide in various concentrations as a raw material. The reaction results, the contents of N-1,3-butadienylacetamide after purification and the polymerizability of the N-vinylacetamide are shown together in Table 1 below.

TABLE 1

| | N-vinyl-acetamide (%) | 33% pH | Conversion (%) | N-Butadienyl-acetamide (ppm) | Polymerizability (cps) |
|---|---|---|---|---|---|
| Example 16 | 3 | 6 | 85 | 2 | 80 |
| Example 17 | 5 | 7 | 84 | 6 | 50 |
| Example 18 | 7 | 8 | 86 | 10 | 30 |
| Example 19 | 1 | 5 | 86 | 10 | 35 |
| Comparative Example 6 | 1 | 4 | 87 | 50 | 8 |
| Comparative Example 7 | 3 | 4 | 87 | 400 | 5 |
| Comparative Example 8 | 11 | 8 | 86 | 40 | 5 |
| Comparative Example 9 | 13 | 8 | 86 | 50 | 5 |

The crude N-vinylacetamide is obtained, for example, (1) by dealcoholization of an N-(1-alkoxyethyl)carboxylic acid amide, (2) by dealcoholization of an N-(1-alkoxyethyl) carboxylic acid amide obtained as an intermediate from carboxylic acid amide, acetaldehyde and alcohol or from carboxylic acid amide and acetaldehyde dialkylacetal, or (3) by cracking ethylidene biscarboxylic acid amide or by cracking an ethylidene biscarboxylic acid amide obtained as an intermediate from acetaldehyde and carboxylic acid amide. The crude N-vinylacetamide obtained by these known production processes does not have good polymerizability. However, when the N-1,3-butadienylcarboxylic acid amide content in the crude N-vinylcarboxylic acid amide is reduced to 30 ppm or less, preferably 10 ppm or less, more preferably 1 ppm or less, and then the crude vinylcarboxylic acid amide is subjected to a purification process, a highly polymerizable N-vinylcarboxylic acid amide having improved polymerizability is obtained.

Furthermore, the N-1,3-butadienylcarboxylic acid amide can be reduced to the above-described content range by subjecting a crude N-vinylcarboxylic acid amide or solution thereof to a purification process such as a rectification method, a recrystallization method, a pressure crystallization method, a physical adsorption method using an activated carbon adsorbent, a Diels-Alder reaction method or a selective hydrogenation reaction method of a 1,3-butadienyl group.

Furthermore, according to the present invention, in producing N-vinylcarboxylic acid amide by thermal cracking or catalytic cracking of N-(1-alkoxyethyl)carboxylic acid amide or ethylidenebiscarboxylic acid amide, a highly polymerizable N-vinylcarboxylic acid amide can be obtained. Furthermore, a polymer of a high molecular weight N-vinylcarboxylic acid amide can be produced using the highly polymerizable monomer.

While the invention has been described in detail and with reference to specific embodiments thereof, it will be apparent to one skilled in the art that various changes and modifications can be made therein without departing from the spirit and scope thereof.

What is claimed is:

1. A homopolymer of N-vinylcarboxylic acid amide or a copolymer thereof with another copolymerizable monomer having a weight average molecular weight of 500,000 or more, prepared by polymerizing a highly polymerizable N-vinylcarboxylic acid amide having an N-1,3-butadienylcarboxylic acid amide content of 30 ppm or less.

2. The product of claim 1, having a weight average molecular weight of 1,000,000 or more.

* * * * *